(12) United States Patent
Song et al.

(10) Patent No.: US 12,144,550 B2
(45) Date of Patent: Nov. 19, 2024

(54) METHOD, APPARATUS, AND DEVICE FOR SIMULATING A TRAVEL PATH OF A CATHETER IN A BLOOD VESSEL

(71) Applicant: Union Strong (Beijing) Technology Co. Ltd., Beijing (CN)

(72) Inventors: Ling Song, Beijing (CN); Xue Feng, Charlottesville, VA (US); Guangming Yang, Beijing (CN); Lan Qin, Beijing (CN)

(73) Assignee: UNION STRONG (BEIJING) TECHNOLOGY CO. LTD., Beijing (CN)

( * ) Notice: Subject to any disclaimer, the term of this patent is extended or adjusted under 35 U.S.C. 154(b) by 686 days.

(21) Appl. No.: 15/734,527

(22) PCT Filed: Oct. 16, 2019

(86) PCT No.: PCT/CN2019/111497
§ 371 (c)(1),
(2) Date: Dec. 2, 2020

(87) PCT Pub. No.: WO2020/078392
PCT Pub. Date: Apr. 23, 2020

(65) Prior Publication Data
US 2021/0228275 A1    Jul. 29, 2021

(30) Foreign Application Priority Data
Oct. 16, 2018   (CN) .......................... 201811204867.3

(51) Int. Cl.
*G06G 7/48*   (2006.01)
*A61B 34/10*  (2016.01)

(52) U.S. Cl.
CPC ........ *A61B 34/10* (2016.02); *A61B 2034/105* (2016.02); *A61B 2034/107* (2016.02)

(58) Field of Classification Search
None
See application file for complete search history.

(56) References Cited

U.S. PATENT DOCUMENTS

| 2002/0137014 | A1   | 9/2002 | Anderson |
| 2008/0160489 | A1 * | 7/2008 | Bruijns .................. G16H 50/50 434/272 |
| 2018/0085167 | A1   | 3/2018 | Goyal |

FOREIGN PATENT DOCUMENTS

| CN | 101128829 A | 2/2008 |
| CN | 103961179 A | 8/2014 |
| CN | 107049487 A | 8/2017 |
| CN | 109199587 A | 1/2019 |
| CN | 109452971 A | 3/2019 |
| CN | 109452972 A | 3/2019 |
| CN | 109512510 A | 3/2019 |
| JP | 2003-030624 A | 1/2003 |
| JP | 2009-226087 A | 10/2009 |

OTHER PUBLICATIONS

Office action issued on Jul. 18, 2023 from Japan Intellectual Property Office in a counterpart Japanese Patent Application No. 2021-503142 (all the cited references are listed in this IDS.) (English translation is also submitted herewith.).

\* cited by examiner

*Primary Examiner* — Anna Skibinsky
(74) *Attorney, Agent, or Firm* — The PL Law Group, PLLC

(57) ABSTRACT

A method, an apparatus, and a device for simulating a travel path of a catheter in a blood vessel. The method comprises: determining a preset path for the catheter to travel in a target artery segment based on extending direction of an artery, wherein the target artery segment refers to an artery segment which is subsequently subjected to catheter path simulation and includes an aneurysm (S101); simulating the travel path of the catheter in a lumen of the target artery segment (S102); and correcting the travel path based on the preset path to obtain a corrected travel path (S103): in this way, the resulting simulated and corrected travel path of the catheter may characterize the actual travel path of the catheter in the artery and may also reflect a substantial shape of the catheter indwelling in the lumen of the artery, wherein the corrected travel path highly agrees with the shape of the artery. Based on the corrected travel path, the travel path of the catheter in the blood vessel and the shape and position of the catheter indwelling in the blood vessel may be determined more accurately, such that the operator may determine more intuitively whether the catheter may be inserted to a specified position in the blood vessel, which enhances convenience. The catheter travels spirally along the arterial wall, ensuring stability of the catheter during a surgery process.

5 Claims, 7 Drawing Sheets

METHOD, APPARATUS, AND DEVICE FOR SIMULATING A TRAVEL PATH OF A CATHETER IN A BLOOD VESSEL

CROSS REFERENCE TO RELATED APPLICATIONS

This application is a national stage application under 35 U.S.C. § 371 of International Application No. PCT/CN2019/111497, filed internationally on Oct. 16, 2019 which claims the benefit of Chinese Application No. 201811204867.3, filed Oct. 16, 2018, the contents of which are incorporated herein by reference in their entirety.

FIELD

The present disclosure relates to computer simulation, and more particularly relates to a method, an apparatus, and a device for simulating a travel path of a catheter in a blood vessel.

BACKGROUND

In the medical field, catheter intervention is a common technology adopted in aneurysm surgeries. According to this technology, a stylet is inserted into an artery; then, a catheter is steered to sleeve outside the stylet; guided by the stylet, the catheter is controlled to pierce through the artery to cause the catheter tip to reach into the aneurysm. After the stylet is extracted, the catheter indwells in the artery. The catheter tip is bent to reach into the aneurysm so as to implement substance transportation, e.g., injecting medicine, spring coil, and etc.; therefore, the position and orientation of the catheter tip have a significant impact on the effect of injecting medicine and etc.

Generally, before catheter intervention, to make the catheter smoothly inserted into the blood vessel, it is needed to determine the travel path of the catheter, causing the travel path of the catheter to substantially agree with the shape of the blood vessel so as to facilitate entry into the blood vessel.

SUMMARY

Embodiments of the present disclosure provide a method, an apparatus, and a device for simulating a travel path of a catheter in a blood vessel so as to solve the problem of poor precision in conventional determination of the travel path of the catheter in the blood vessel.

The present disclosure provides a method for simulating a travel path of a catheter in a blood vessel, comprising:
  determining a preset path for the catheter to travel in a target artery segment based on extending direction of an artery, wherein the target artery segment refers to an artery segment which is subsequently subjected to catheter path simulation and includes an aneurysm;
  simulating the travel path of the catheter in a lumen of the target artery segment; and
  correcting the travel path based on the preset path to obtain a corrected travel path;

The present disclosure further provides an apparatus for simulating a travel path of a catheter in a blood vessel, comprising:
  a preset path determining module configured for determining a preset path in the lumen of an aneurysm segment to simulate a catheter travel path based on extending direction of an artery, wherein the aneurysm segment to simulate a catheter travel path refers to an artery segment including the aneurysm to simulate the catheter travel path;
  a simulating module configured for simulating the travel path of the catheter in a lumen of the target artery segment; and
  a correcting module configured for correcting the travel path based on the preset path to obtain a corrected travel path.

The present disclosure provides an electronic device, comprising: at least one processor and a memory, the memory storing a program which, when being executed by the at least one processor, performs the steps below:
  determining a preset path for the catheter to travel in a target artery segment based on extending direction of an artery, wherein the target artery segment refers to an artery segment which is subsequently subjected to catheter path simulation and includes an aneurysm;
  simulating the travel path of the catheter in a lumen of the target artery segment; and
  correcting the travel path based on the preset path to obtain a corrected travel path.

The present disclosure provides a computer-readable storage medium, comprising a program used in combination with the electronic device, wherein the program may be executed by the processor to perform the steps below:
  determining a preset path for the catheter to travel in a target artery segment based on extending direction of an artery, wherein the target artery segment refers to an artery segment which is subsequently subjected to catheter path simulation and includes an aneurysm;
  simulating the travel path of the catheter in a lumen of the target artery segment; and
  correcting the travel path based on the preset path to obtain a corrected travel path;

At least one of the technical solutions above adopted in the embodiments of the present disclosure may achieve the following beneficial effects:

In the embodiments of the present disclosure, the method for simulating a travel path of a catheter in a blood vessel comprises steps of: determining a preset path for the catheter to travel in a target artery segment based on extending direction of an artery, wherein the target artery segment refers to an artery segment which is subsequently subjected to catheter path simulation and includes an aneurysm; simulating the travel path of the catheter in a lumen of the target artery segment; and correcting the travel path based on the preset path to obtain a corrected travel path; in this way, the resulting simulated and corrected travel path of the catheter may characterize the actual travel path of the catheter in the artery and may also reflect a substantial shape of the catheter indwelling in the lumen of the artery, wherein the corrected travel path highly agrees with the shape of the artery, and the travel path maintains consistency with the morphology of the artery in the three-dimensional space, e.g., when the artery has a spiral shape, the catheter may travel spirally and upwardly in adhesion to the arterial wall. Based on the corrected travel path, the travel path of the catheter in the blood vessel and the shape and position of the catheter indwelling in the blood vessel may be determined more accurately, such that the operator may determine more intuitively whether the catheter may be inserted to a specified position in the blood vessel, which enhances convenience.

BRIEF DESCRIPTION OF THE DRAWINGS

The drawings illustrated herein are used for providing further understanding of the present disclosure, which constitute part of the present disclosure. The illustrative embodiments of the present disclosure and descriptions thereof are used for explaining the present disclosure, which do not constitute improper limitations to the present disclosure. In the drawings.

DETAILED DESCRIPTION OF EMBODIMENTS

Figure 1:
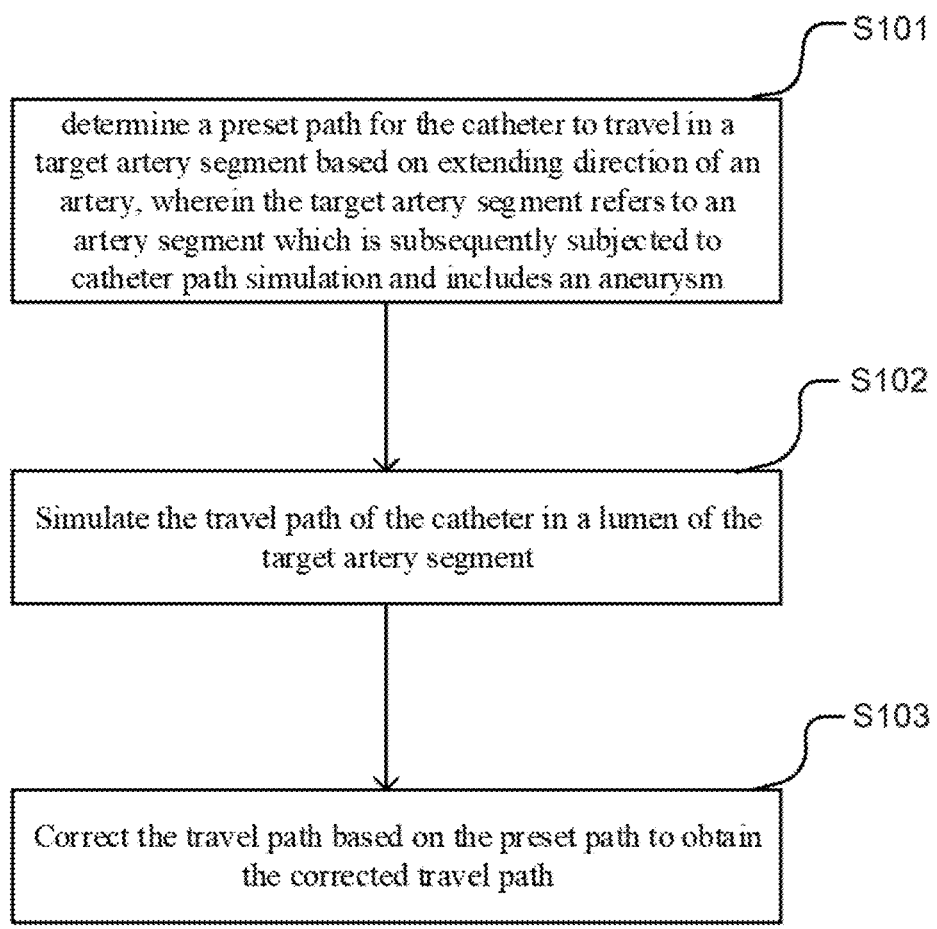
FIG. 1 shows a flow diagram of a method for simulating a travel path of a catheter in a blood vessel according to an embodiment of the present disclosure.

Analysis of the prior art finds that when determining the shaping of a catheter, a physician would contemplate the three-dimensional shape of the artery based on its two-dimensional shape, determine the bend, the bend direction, and the bend angle of the to-be-shaped catheter based on subjective measurements, and then shape the catheter based on the measured bend, bend direction and bend angle. However, this solution relies on the subjective measurement of physicians, which is largely affected by random factors, such that shaping of the catheter cannot be determined accurately.

An embodiment of the present disclosure provides a method for simulating the shape of a catheter, which may obtain a corrected travel path by simulating the travel path of the catheter in the lumen of an aneurysm segment to simulate a catheter travel path and then correcting the travel path based on a preset path in the lumen of the aneurysm segment to simulate a catheter travel path. In the embodiments of the present disclosure, the method for simulating a travel path of a catheter in a blood vessel comprises steps of: determining a preset path for the catheter to travel in a target artery segment based on extending direction of an artery, wherein the target artery segment refers to an artery segment which is subsequently subjected to catheter path simulation and includes an aneurysm; simulating the travel path of the catheter in a lumen of the target artery segment; and correcting the travel path based on the preset path to obtain a corrected travel path; in this way, the resulting simulated and corrected catheter path may characterize the actual travel path of the catheter in the artery and may also reflect a substantial shape of the catheter indwelling in the lumen of the artery, wherein the corrected travel path highly agrees with the shape of the artery, and the travel path maintains consistency with the morphology of the artery in the three-dimensional space, e.g., when the artery has a spiral shape, the catheter may travel spirally and upwardly in adhesion to the arterial wall. Based on the corrected travel path, the travel path of the catheter in the blood vessel and the shape and position of the catheter indwelling in the blood vessel may be determined more accurately, such that the operator may determine more intuitively whether the catheter may be inserted to a specified position in the blood vessel, which enhances convenience.

To make the objects, technical solutions, and advantages of the present disclosure more apparent, the technical solutions of the present disclosure will be described in a clear and comprehensive fashion with reference to the embodiments and corresponding drawings of the present disclosure. Apparently, the embodiments described herein are only part of the embodiments of the present disclosure, not all of them. All other embodiments, obtained by those skilled in the art based on the embodiments in the present disclosure without exercise of inventive work, shall fall within the protection scope of the present disclosure.

FIG. 1 shows a flow schematic diagram of a method for simulating a travel path of a catheter in a blood vessel according to an embodiment of the present disclosure, comprising:

Step 101: determining a preset path for the catheter to travel in a target artery segment based on extending direction of an artery, wherein the target artery segment refers to an artery segment which is subsequently subjected to catheter path simulation and includes an aneurysm.

It is to be noted that the target artery segment may also be referred to as a to-be-simulated aneurysm segment.

In the embodiments of the present disclosure, the aneurysm segment to simulate a catheter travel path may be a model built based on the actual vessel shape. Specifically, the aneurysm segment to simulate a catheter travel path may be an aneurysm segment to simulate a catheter travel path of three-dimensional morphology, because the aneurysm segment to simulate a catheter travel path of three-dimensional morphology may reflect the vessel morphology more truly.

Particularly, the artery segment of the aneurysm may include a partial segment from the catheter entry on the artery to the aneurysm and the aneurysm connected to the partial segment.

In this way, the determining a preset path for the catheter to travel in a target artery segment based on extending direction of an artery comprises:

determining the target artery segment of a three-dimensional shape based on the extending direction of the artery; and determining the preset path in the lumen of the target artery segment of the three-dimensional shape.

In this embodiment, to determine the target artery segment of a three-dimensional shape, the artery may be subjected to three-dimensional segmentation, and then the three-dimensional model of the artery is reconstructed. The algorithms and technologies for three-dimensional segmentation of the artery may include: a pattern recognition technology, a model-based method, a tracking-based method, an artificial intelligence method, and a neural network method, etc., which are not specifically limited here.

In the embodiment of the present disclosure, the preset path may serve as a baseline for subsequently correcting the simulated travel path of the catheter. To make the travel path highly agree with the arterial shape, the preset path may be a path along the centerline of the aneurysm segment to simulate a catheter travel path; or a path deviating a certain distance from the centerline of the aneurysm segment to simulate a catheter travel path, such that the preset path may be parallel to or collide with the centerline of the aneurysm segment to simulate a catheter travel path.

In an embodiment of the present disclosure, the determining a preset path for the catheter to travel in a target artery segment based on extending direction of an artery may further comprise:

determining an intervention segment between the catheter entry on the artery and the aneurysm;

determining the preset path in the lumen of the target artery segment for the intervention segment based on the extending direction of the artery.

In an actual operation, the catheter is inserted into the artery via the entry formed on the artery, wherein the intervention segment may refer to the catheter portion which is connected with the catheter tip portion and inserted into the artery after the catheter tip portion is inserted into the aneurysm. Here, the purpose of determining the preset path in the lumen of the target artery segment for the intervention segment is to finally simulate the shape of the portion of the catheter corresponding to the intervention segment, which may further enhance stability of the catheter in the artery.

S102: simulating the travel path of the catheter in a lumen of the target artery segment.

In the embodiments of the present disclosure, by simulating the travel path of the catheter, the travel path of the catheter inserted into the artery in an actual scene may be simulated and the substantial shape of the catheter in the artery may be obtained. Here, the travel path of the catheter may be simulated using the lumen of the pre-constructed aneurysm segment to simulate a catheter travel path.

In the embodiments of the present disclosure, simulating the travel path of the catheter in a lumen of the target artery segment may comprise:

simulating, segment by segment, simulating the travel path of the catheter in a lumen of the target artery segment based on preset segments.

In an actual scene, when the catheter is travelling in the artery, the catheter tip travels along a preset path; when it collides with the arterial wall, it will make a turn and continue travelling; therefore, the whole travel path is actually segmented. In light of this actual scene, the embodiments of the present disclosure implement simulating, segment by segment in sequence, the travel path of the catheter in a lumen of the target artery segment based on preset segments.

In the embodiments of the present disclosure, the length of each preset segment may be set randomly or set based on the actual artery scene, which are not specifically limited here. During the simulation process, the preset segments may be fixedly set or may vary from time to time with the travel path, which are not specifically limited here.

Figure 2:
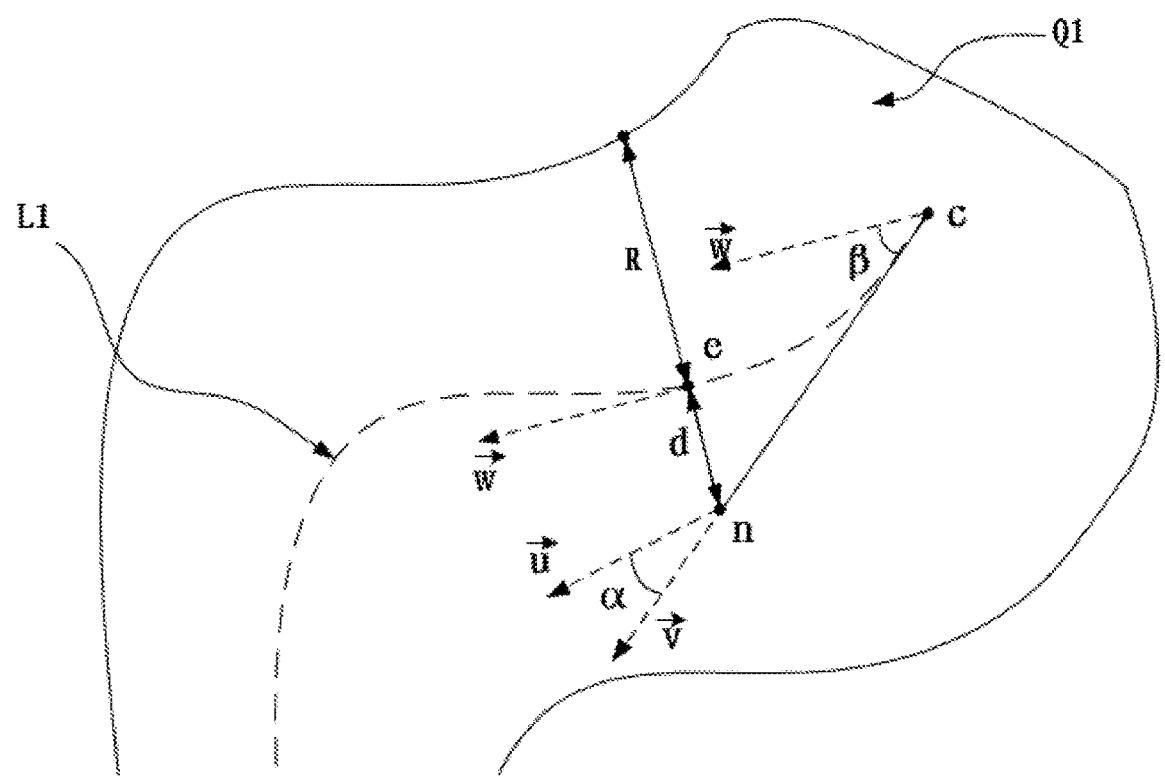
FIG. 2 shows a principle schematic diagram of a method for simulating a travel path of a catheter in a blood vessel according to an embodiment of the present disclosure.

FIG. 2 shows a principle schematic diagram of a method for simulating a travel path of a catheter in a blood vessel according to an embodiment of the present disclosure, where Q1 denotes the lumen of the aneurysm segment to simulate a catheter travel path; L1 denotes the preset path; c-n may represent any preset segment as simulated, wherein c denotes the start position of the preset segment, n denotes the end position of the preset segment, and $\vec{V}$ denotes the travel direction of the preset segment.

In the embodiments of the present disclosure, the start point of the travel path may be determined based on the start point of the preset path or determined based on a point at another position in the lumen of the aneurysm segment to simulate a catheter travel path, which are not specifically limited here.

The preset segment may serve as a section of the simulated travel path, and the travel path corresponding to the next preset segment may be simulated based on the preset segment. Specifically, the start position of the next preset segment may be determined from the end position n of the preset segment, and the travel direction of the next preset segment may be determined from the travel path of the preset segment; in this way, the next preset segment may be simulated. Following this principle, simulating, segment by segment in sequence, the travel path of the catheter in a lumen of the target artery segment based on the preset segments may be implemented.

S103: correcting the travel path based on the determined preset path.

In the embodiments of the present disclosure, in an actual scene, the catheter does not travel in the artery precisely along a preset path; instead, it always deviates from the preset path, such that its travel trajectory is in a constantly changing process. In this way, when simulating the travel path of the catheter in a lumen of the target artery segment, the simulated travel path possibly deviates from the preset path; therefore, it is needed to correct the simulated travel path so as to ensure that the deviation between the travel path and the preset path is as small as possible.

With reference to step S102, if the travel path of the catheter in the lumen of the aneurysm simulated segment is simulated, segment by segment in sequence, based on preset segments, the correcting the travel path based on the preset path may comprise:

correcting each of the preset segments based on the preset path.

During the simulation process, after one preset segment is simulated, the travel path of the preset segment may be immediately corrected, and then the next preset segment is simulated and corrected. Alternatively, the entire travel path may be first simulated, and then correction is made to respective preset segments. The present disclosure has no specific limitation thereto.

In this case, the corrected preset segment acts as a portion of the finally simulated travel path.

In the embodiments of the present disclosure, the correcting each of the preset segments based on the preset path may comprise:

determining an end position of the preset segment based on the travel direction of the preset segment; and correcting at least one of the end position and the travel direction of the end position based on the deviation between the end position and the preset path.

During the correcting process, the correcting at least one of the end position and the travel direction of the end position based on the deviation between the end position and the preset path may comprise:

determining the deviation between the end position of the preset segment and the preset path;

determining whether the deviation from the preset path exceeds a threshold;

in the case of No, determining to simulate the travel path corresponding to the next preset segment;

in the case of Yes, determining to correct the preset segment corresponding to the end position and simulate the travel path corresponding to the next preset segment based on the corrected preset segment.

Specifically, the correcting at least one of the end position and the travel direction of the end position based on the deviation between the end position and the preset path may comprise:
  if the end position is within the scope of the lumen of the aneurysm segment to simulate a catheter travel path while its deviation from the preset path exceeds the threshold, correcting the travel direction of the end position.
  if the current end position is still within the scope of the lumen of the aneurysm segment to simulate a catheter travel path while its deviation from the preset path does not exceed the threshold, it indicates that the end position of the preset segment may serve as the start position of the next preset segment. However, if the deviation of the end position of the current preset segment from the preset path exceeds the threshold, it indicates that there is a relatively large deviation between the current preset segment and the preset path; in this case, if the next preset segment were still simulated based on the travel direction of the current preset segment, there would be a high likelihood that the next preset segment would collide with the lumen wall of the aneurysm segment to simulate a catheter travel path or travel beyond the scope of the lumen of the aneurysm segment to simulate a catheter travel path. In this case, by correcting the simulated travel direction of the current preset segment and simulating the next preset segment based on the corrected travel direction, the next preset segment may be close to the preset path, or the deviation from the preset path does not exceed the threshold, or preset segment does not travel beyond the scope of the lumen.

In the embodiments of the present disclosure, the threshold may be set according to needs, which is not specifically limited here. That the end position is within the scope of the lumen of the aneurysm segment to simulate a catheter travel path may refer to:
  the end position being located between the lumen wall of the lumen and the preset path;
or refer to:
  the end position being located at the lumen wall of the lumen.

In the embodiments of the present disclosure, that the deviation of the end position from the preset path exceeds a threshold may refer to the distance from the end position of the preset segment to a specified point on the preset path exceeding the threshold, wherein the distance from the end position of the preset segment to the specified point on the preset path is used to characterize the deviation degree between the end position of the preset segment and the preset path. Particularly, because the distance from the end position to the specified point is shorter than those distances from the end position to other points on the preset path, the specified point refers to the point closest to the end position on the preset path. During the process of simulating the entire travel path, the specified point is always in a changing condition.

In the embodiments of the present disclosure, deviation of the end position from the preset path may also be characterized by a ratio between the distance from the end position to the specified point on the preset path and the radius of the artery; the larger the ratio is, the greater the deviation between the end position and the preset path is.

In this case, the principle of correcting the preset segment may refer to FIG. 2, where e denotes the specified point on the preset path L1, wherein because the distance d between the end position n of the preset segment c-n and e is shorter than the distances to other points on the preset path L1, e denotes the point closest to n on L1; R denotes the radius of the artery, $\vec{w}$ denotes the tangent line direction of the preset path L1 at point e; β denotes the included angle between the travel direction $\vec{v}$ of the preset segment c-n and $\vec{w}$, wherein $\vec{u}$ denotes the travel direction obtained from correcting $\vec{v}$, and α denotes the included angle between the travel direction $\vec{v}$ at the end position n and the corrected travel direction $\vec{u}$. In this way, $\vec{u}$ may be determined by calculating α.

In FIG. 2, d exceeds the threshold; then the deviation of n from L1 within the scope of Q1 exceeds the threshold; in this case, the travel direction of n may be corrected according to the centerline constraint principle below.

As such, if the end position is located within the scope of the lumen of the aneurysm segment to simulate a catheter travel path and the deviation from the preset path exceeds the threshold, the correcting the travel direction of the end position may comprise:
  determining the included angle between the travel direction $\vec{v}$ of the end position and the corrected travel direction $\vec{u}$ based on the equation below:

$$\alpha = \varphi \mathrm{sigmoid}(\beta/\pi, \alpha 1, \beta 1) + \mathrm{sigmoid}(d/R, \alpha 2, \beta 2));$$

where φ denotes an empirical constant value of the angle;
  d denotes the distance from the end position to the specified point on the preset path;
  R denotes the radius of the artery;
  β denotes the included angle between the travel direction of the end position and the tangent line direction at the specified point on the preset path;
  sigmoid $$(\beta/\pi, \alpha 1, \beta 1) = \frac{1}{1 + e^{\frac{\alpha_1 - \beta/\pi}{\beta_1}}},$$

α1 is the empirical constant value corresponding to α, and β1 is the empirical constant value corresponding to β;
  sigmoid $$(d/R, \alpha 2, \beta 2) = \frac{1}{1 + e^{\frac{\alpha_2 - d/R}{\beta_2}}},$$

where α2 is the empirical constant value corresponding to α, and β is the empirical constant value corresponding to β,
    wherein φ denotes the base angle of the included angle between the travel direction of the end position and the corrected travel direction; when φ takes a larger value, the corrected travel path is closer to the preset path; when φ takes a smaller value, the corrected travel path is closer to the lumen wall of the aneurysm segment to simulate a catheter travel path.

After the included angle α between the current travel direction $\vec{v}$ and the corrected travel direction $\vec{u}$ is determined, the travel direction $\vec{v}$ of the end position n is immediately corrected based on α to obtain the corrected travel direction $\vec{u}$, as shown by the travel direction $\vec{u}$ in FIG. 2.

Figure 3:
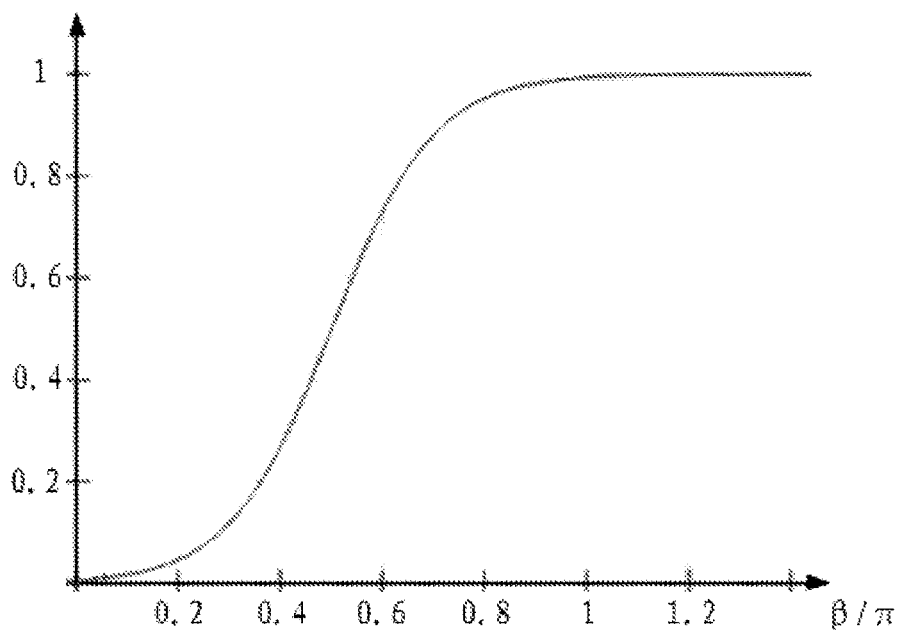
FIG. 3 shows a principle schematic diagram of a method for simulating a travel path of a catheter in a blood vessel according to an embodiment of the present disclosure.

Particularly, for sigmoid $$(\beta/\pi, \alpha1, \beta1) = \frac{1}{1+e^{\frac{\alpha_1-\beta/\pi}{\beta_1}}},$$

please refer to FIG. 2 and FIG. 3 in combination, wherein FIG. 3 shows a principle schematic diagram of a method for simulating a travel path of a catheter in a blood vessel according to an embodiment of the present disclosure. The coordinate system shown in FIG. 3 is a function image with $\beta/\pi$ as the transverse coordinate and sigmoid ($\beta\pi$, $\alpha1$, $\beta1$) as the longitudinal coordinate, where $\alpha1=0.5$, $\beta1=0.1$; in this way, the coordinate system shown in FIG. 3 represents a curve where $\alpha$ changes with $\beta$, indicating that the included angle $\alpha$ between the current travel direction $\vec{v}$ and the corrected travel direction $\vec{u}$ increases as $\beta$ increases. The slope of the function image represents the sensitive degree of the variation of the included angle $\alpha$ between $\vec{v}$ and $\vec{u}$ with $\beta$.

Figure 4:
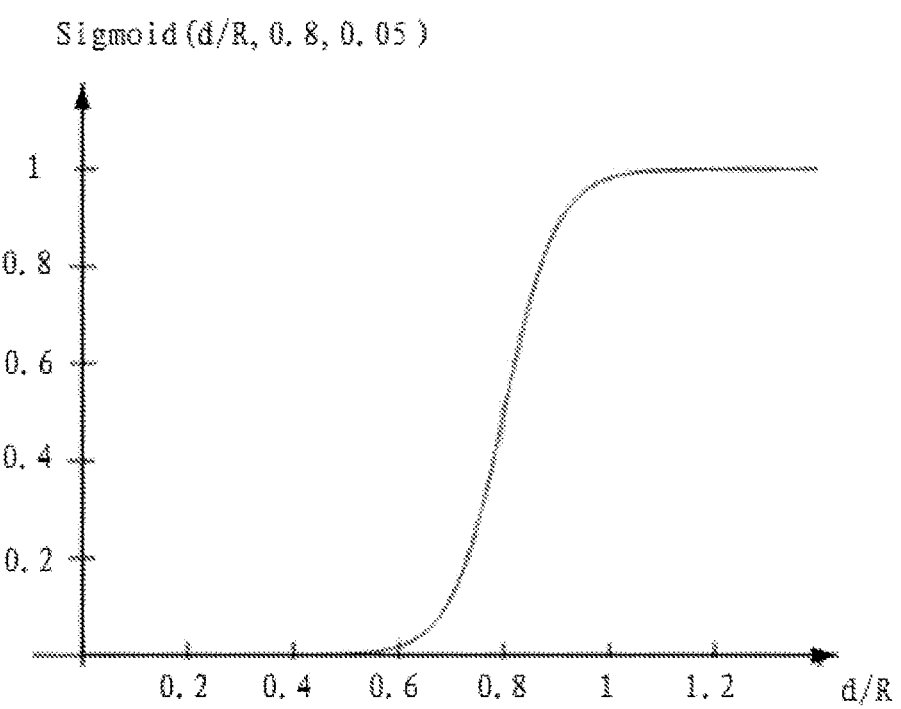
FIG. 4 shows a principle schematic diagram of a method for simulating a travel path of a catheter in a blood vessel according to an embodiment of the present disclosure.

In the image shown in FIG. 3, when $\beta/\pi$ is less than $\alpha1$, the slope increases as $\beta$ increases; when $\beta/\pi$ is greater than $\alpha1$, the slope decreases as $\beta$ increases, where $\alpha1=0.5$, $\beta1=0.1$, indicating $\beta=\pi/2$, Particularly, for sigmoid $$(d/R, \alpha2, \beta2) = \frac{1}{1+e^{\frac{\alpha_2-d/R}{\beta_2}}},$$

please refer to FIG. 2 and FIG. 4 in combination, wherein FIG. 4 shows a principle schematic diagram of a method for simulating a travel path of a catheter in a blood vessel according to an embodiment of the present disclosure. The coordinate system shown in FIG. 4 indicates a function image with d/R as the transverse coordinate and sigmoid (d/R,$\alpha2$,$\beta2$) as the longitudinal coordinate. where $\alpha2=0.8$, $\beta2=0.05$; as such, the coordinate system shown in FIG. 4 indicates the curve of variation of $\alpha$ with d, wherein the curve indicates that $\alpha$ increases as d increases. The slope of the function image indicates the sensitive degree of variation of $\alpha$ with d.

By adjusting the values of $\varphi$, $\alpha1$, $\beta1$, $\alpha2$, and $\beta2$, a desired travel path may be obtained based on the specific scenario of the aneurysm segment to simulate a catheter travel path.

By virtue of the technical solution described in the embodiments of the present disclosure, the travel direction of the end position is corrected based on the deviation between the end position of each preset segment and the preset path. Therefore, the specific expressions of the equations above are only embodiments of the present disclosure, not for limiting the present disclosure.

In the embodiments of the present disclosure, the correcting at least one of the end position and the travel direction of the end position based on the deviation between the end position and the preset path may comprise:

if the end position is located outside the lumen of the aneurysm segment to simulate a catheter travel path, correcting the end position and the travel direction of the end position till the end position is located within the scope of the lumen of the aneurysm segment to simulate a catheter travel path;

if the end position is located outside the lumen of the aneurysm segment to simulate a catheter travel path, it deviates from the actual scene; therefore, the end position is corrected within the scope of the lumen of the aneurysm segment to simulate a catheter travel path.

In the embodiments of the present disclosure, the correcting the end position and the travel direction of the end position till the end position is located within the scope of the lumen of the aneurysm segment to simulate a catheter travel path may comprise:

correcting the end position to the lumen wall of the lumen.

At this point, the lumen wall of the lumen is the boundary of the lumen of the aneurysm segment to simulate a catheter travel path, which is for limiting the scope of the lumen of the aneurysm segment to simulate a catheter travel path and thus may be regarded as a portion of the scope of the lumen of the aneurysm segment to simulate a catheter travel path.

If the end position of the preset segment is located outside the lumen of the aneurysm segment to simulate a catheter travel path, it indicates that the current preset segment reaches the position where the corresponding artery has a relatively large bend degree, and the curvature at the intersection position between the aneurysm segment to simulate a catheter travel path and the preset segment is relatively large. By correcting the end position to the lumen wall of the lumen, the corrected travel path may form a knee point at the end position and thus has a relatively large curvature. With shaping of the knee point, the catheter shaped based on the corrected travel path plays a good support role at the knee point position.

In this case, the travel path of the next preset segment, which is simulated with the corrected end position on the lumen wall as the start position of the next preset and the travel direction of the corrected end position as the travel direction of the next preset segment, agrees with the travel path of the catheter in the real artery environment.

In actual applications, correcting the end position to the lumen wall of the lumen may comprise:

rotating, with the start position of the preset segment as the rotating center, the preset segment till the end position is located on the lumen wall of the lumen along the direction of gradually approaching to the preset path.

The purpose of rotating the preset segment along the direction of approaching to the preset path is to ensure that the travel direction of the corrected end position will not deflect 180° (i.e., reversed).

In the embodiments of the present disclosure, the rotating the preset segment till the end position is located on the lumen wall of the lumen may comprise:

when determining a normal vector of the intersection position between the lumen wall of the lumen and the preset segment, determining a rotating plane based on the normal vector and the travel direction of the preset segment;

in the rotating plane, rotating, with the start position of the preset segment as the rotating center, the preset segment till the end position is located on the lumen wall of the lumen along the direction of gradually approaching to the preset path.

Corresponding to the shape of a real artery, the aneurysm segment to simulate a catheter travel path described in the embodiments of the present disclosure has a spiral shape; the intersection position between the lumen wall of the lumen and the preset segment may correspond to a position where the lumen wall has a relatively large curvature; therefore, by determining the rotating plane based on the normal vector, the rotation trajectory is the shortest when the preset segment rotates along the direction of gradually approaching the preset path.

Meanwhile, the corrected travel path may maintain consistency with the morphology of the aneurysm segment to simulate a catheter travel path in the three-dimensional space; for example, when the aneurysm segment to simulate a catheter travel path has a spiral shape, the corrected travel path may also have a spiral shape; therefore, when the catheter determined based on this corrected travel path is traveling in the artery, it may be bent to fit with the shape of the artery so as to enter the artery more easily.

Figure 5:
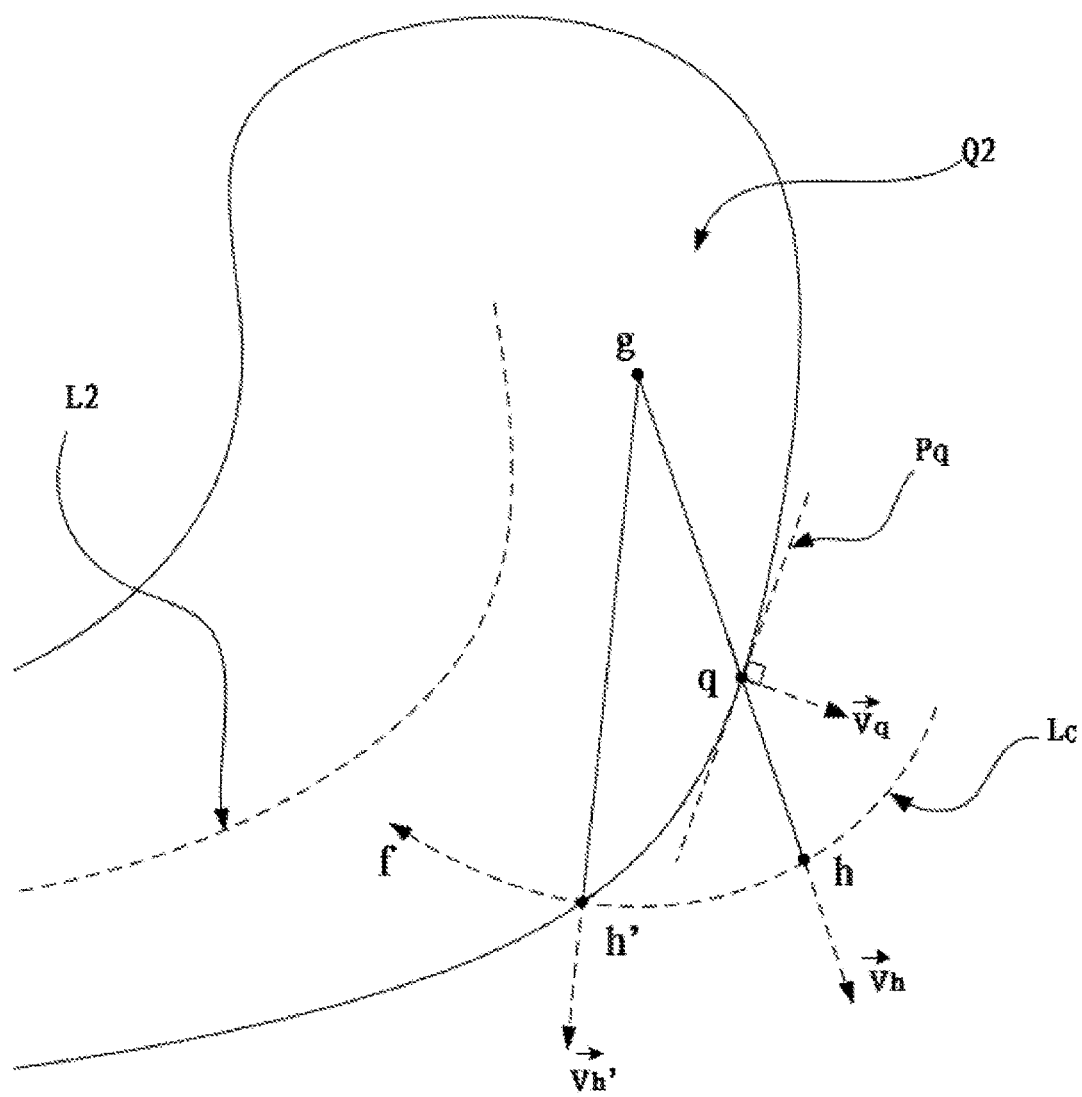
FIG. 5 shows a principle schematic diagram of a method for simulating a travel path of a catheter in a blood vessel according to an embodiment of the present disclosure.

Now, refer to FIG. 5, which shows a principle schematic diagram of a method for simulating a travel path of a catheter in a blood vessel according to an embodiment of the present disclosure, specifically showing the correction principle schematic diagram when the end position of the preset segment is located outside the lumen.

As shown in FIG. 5, Q2 denotes the lumen of the aneurysm segment to simulate a catheter travel path; L2 denotes the preset path; g-h denotes the current simulated preset segment, g denotes the start position of the preset segment; h denotes the end position of the preset segment; the travel direction of g-h is $\vec{v}h$; q denotes the intersection point between the preset segment g-h and the lumen wall of Q2; Pq denotes the tangent plane of Q2 at q; and $\vec{v}q$ denotes the normal vector of the tangent plane.

The specific correction principle may be described as follows: determining the rotating plane based on $\vec{v}q$ and $\vec{v}h$; in the rotating plane, the preset segment g-h is rotated with g as the rotating center to obtain the motion trajectory $L_c$ of the end position, such that the end position is rotated from h to h', wherein h' is located on the lumen wall, and $\vec{v}h$ is the travel direction of the corrected end position h'.

In this way, the corrected preset segment g-h' serves as a portion of the final travel path.

Next, the travel path of the next preset segment may be simulated based on the corrected end position h' and the travel direction $\vec{v}h$ of the corrected end position.

If the end position of the next preset segment is still located outside the scope of the lumen of the aneurysm segment to simulate a catheter travel path, the end position of the next preset segment and the travel direction of the end position may be corrected using the correction principle applicable for the scenario where the end position of the preset segment is located outside the lumen, as shown in FIG. 5, which will not be detailed here. If the end position of the next preset segment is located within the scope of the lumen of the aneurysm segment to simulate a catheter travel path, the travel direction of the end position may be corrected based on the above centerline constraint principle, which will not be detailed here.

In the embodiments of the present disclosure, the correcting the end position and the travel direction of the end position till the end position is located within the scope of the lumen of the aneurysm segment to simulate a catheter travel path may comprise:

correcting the end position till being located within the scope of the lumen such that the deviation from the preset path is less than the threshold.

During this process, specifically, the correcting the end position till being within the scope of the lumen such that the deviation from the preset path is less than the threshold may comprise:

rotating, about the start position of the preset segment along a direction of gradually approaching to the preset path, the preset segment till the end position is within the scope of the lumen such that the deviation from the preset path is less than the threshold.

The specific correction principle may be described as follows: rotating the preset segment along the direction of gradually approaching to the preset path till the minimal distance from the end position to the preset path is less than a threshold. During this process, the minimal distance from the end position to the preset path may be computed in real time till obtaining that the minimal distance is less than the threshold.

In the embodiments of the present disclosure, when the end position of the current preset segment is located outside the lumen of the aneurysm segment to simulate a catheter travel path, if there still exists a portion of the preset segment which is located within the scope of the lumen, the correcting the end position and the travel direction of the end position may comprise:

narrowing the preset segment till being located within the scope of the lumen along an inverse direction to the travel direction of the preset segment.

In the embodiments of the present disclosure, after at least one of the end position and the travel direction of the end position is corrected based on the deviation between the end position and the preset path, the simulating, segment by segment in sequence, the travel path of the catheter in a lumen of the target artery segment based on the preset segments may comprise:

determining a start position of a to-be-simulated preset segment based on the corrected end position;
determining the travel direction of the to-be-simulated preset segment based on the corrected travel direction of the end position; and
simulating the travel path of the catheter in the to-be-simulated preset segment based on the determined start position and the determined travel direction of the to-be-simulated preset segment.

in the embodiments of the present disclosure, considering that the preset path in the artery aneurysm has a limited length, the simulating the travel path of the catheter in a lumen of the target artery segment may comprise:

simulating the travel path of the catheter in the aneurysm segment to simulate a catheter travel path till the length of the corrected travel path exceeds the length of the preset path.

Figure 6:
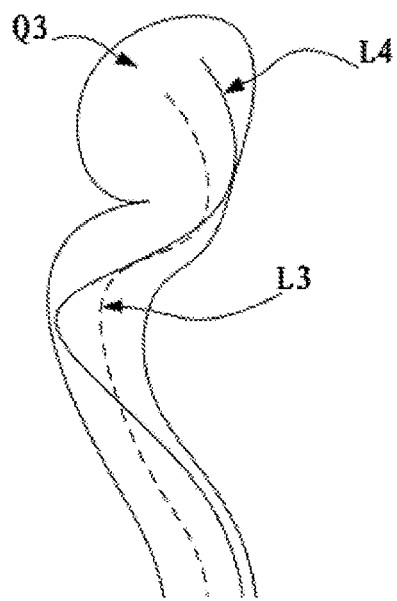
FIG. 6 shows an effect diagram of the method for simulating a travel path of a catheter in a blood vessel according to an embodiment of the present disclosure.

Through steps S101~S103, the simulated travel path of the catheter may be obtained, as specifically shown in FIG. 6, which shows an effect diagram of the method for simulating a travel path of a catheter in a blood vessel according to an embodiment of the present disclosure, specifically illustrating the catheter travel path obtained based on the method of simulating the shape of catheter as described in the embodiments of the present disclosure, where Q3 denotes the lumen of the aneurysm segment to simulate a catheter travel path, 13 denotes the preset path, L4 denotes the corrected travel path; as shown in FIG. 6, within a permissible extent, the corrected travel path substantially agrees with the preset path; in this way, when the catheter determined based on the corrected travel path indwells in the artery, a good stability may be provided.

The process of the catheter entering the artery may be simulated based on the corrected travel path, such that the travel path of the catheter in the artery and the shape and position of the catheter indwelling in the artery may be determined more accurately, such that the operator may determine more intuitively whether the catheter may be inserted to a specified position in the artery, which enhances convenience.

When the corrected travel path is obtained, catheter intervention may be simulated based on the corrected travel path, and the shape of the catheter may also be determined based on the corrected travel path.

In the embodiments of the present disclosure, on the basis of correcting the travel path of the catheter, the shape of the catheter may be determined based on the corrected travel path. In this way, the preset path in the lumen of the aneurysm segment to simulate a catheter travel path is determined based on the extending direction of the artery;

the travel path of the catheter in a lumen of the target artery segment is simulated; and the travel path is corrected based on the preset path to obtain the corrected travel path.

The method for simulating a travel path of catheter in a blood vessel may further comprise: determining the shape of the catheter based on the corrected travel path. In the embodiments of the present disclosure, by determining the shape of the catheter based on the corrected travel path, the bend, as well as the bend angle and the bend direction of the bend, may be precisely determined, thereby better fitting with the morphology of the artery aneurysm simulated segment.

In the embodiments of the present disclosure, the determining the shape of the catheter based on the corrected travel path may comprise:

processing the travel path and determining the bend angle of at least one bend part of the catheter along an extending direction of the catheter.

The bend part refers to a bend of the catheter when shaping the catheter; the corrected travel path may reflect the substantial shape of the catheter indwelling in the lumen of the artery; therefore, the bend angle of the at least one bend along the extending direction of the artery may be determined based on the corrected travel path.

Particularly, determining a bend angle of at least one bend of the catheter along the extending direction of the catheter may comprise:

determining the bend angle and the bend direction of the at least one bend of the catheter along the extending direction of the catheter.

Therefore, in the embodiments of the present disclosure, the determining a bend angle of at least one bend of the catheter along the extending direction of the catheter may comprise:

determining a target point distributed along the corrected travel path; and determining the bend angle of the bend based on the bend angle formed by the corrected travel path at the target point.

In the embodiments of the present disclosure, the bend angle formed by the corrected travel path at the target point refers to the included angle between the travel direction when the travel path advances to the target point and the corrected travel direction. In this way, the determining the bend angle of the bend based on the bend angle formed by the corrected travel path at the target point may comprise:

determining the bend direction of the bend based on the deflection direction of the travel direction when the corrected travel path approaches to the target point from the corrected travel direction; and determining the bend angle of the bend based on the included angle between the travel direction when the corrected travel path travels to the target point and the corrected travel direction.

Particularly, the deflection direction of the travel direction when the corrected travel path travels to the target point from the corrected travel direction follows the right hand grip rule, which may be specifically determined based on the cross product of the vector of the travel direction when the corrected travel path travels to the target point and the vector of the corrected travel direction.

Particularly, the determining the bend angle of the bend based on the included angle between the travel direction when the corrected travel path travels to the target point and the corrected travel direction may comprise:

directly determining the bend angle formed by the corrected travel path at the target point as the bend angle of the bend.

In the embodiments of the present disclosure, considering that the catheter inherently has elasticity, which might rebound after being shaped, the determined bend angle of the bend may be greater than the bend angle formed by the corrected travel path at the target point. At this point, the determining the bend angle of the bend based on the bend angle formed by the corrected travel path at the target point may comprise:

determining the bend angle of the bend based on the bend angle formed by the corrected travel path at the target point and the rebound rate of the catheter during the shaping process.

Figure 7:
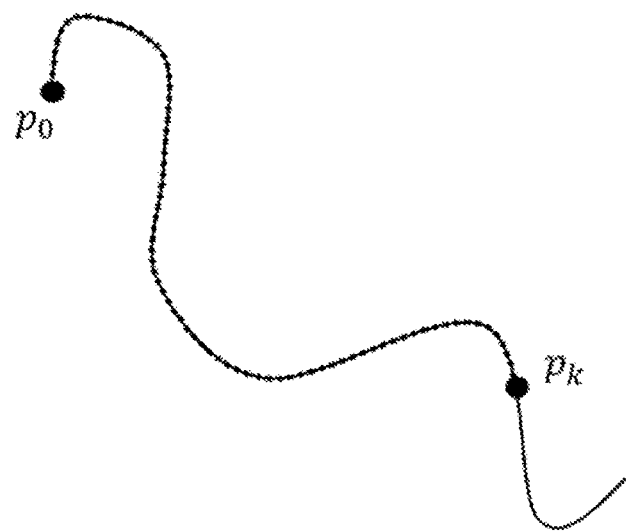
FIG. 7 shows a principle schematic diagram of a method for simulating a travel path of a catheter in a blood vessel according to an embodiment of the present disclosure.

Specifically, refer to FIG. 7, which shows a principle schematic diagram of a method for simulating a travel path of a catheter in a blood vessel according to an embodiment of the present disclosure, specifically illustrating the schematic diagram of the corrected travel path resulting from steps S101~S103, wherein a plurality of target points between $p_0$ and $p_k$ on the travel path may be selected, and then a plurality of bend angles formed at the plurality of target points are determined.

Figure 8:
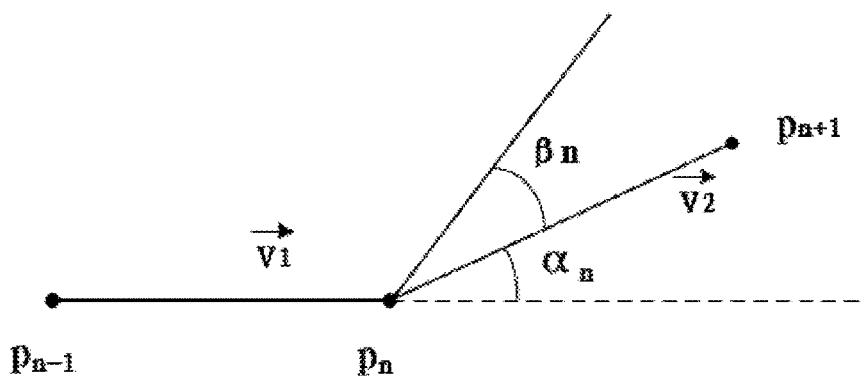
FIG. 8 shows a principle schematic diagram of a method for simulating a travel path of a catheter in a blood vessel according to an embodiment of the present disclosure.

Refer to FIG. 8, which shows a principle schematic diagram of a method for simulating a travel path of a catheter in a blood vessel according to an embodiment of the present disclosure, specifically illustrating that the bend angle $\alpha_n$ formed by the corrected travel path at the target point $p_n$ refers to the included angle between the travel direction $\vec{v}1$ when the travel path advances to the target point $p_n$ and the corrected travel direction $\vec{v}2$, representing the deflection degree (or deflection angle) of the travel direction when the travel path advances to the target point $p_n$, where $\beta_n+\alpha_n$ represents the determined bend angle of the bend, and $\beta_n$ represents the bend angle determined based on the material and the rebound rate of the catheter, which are not specifically limited here.

In the embodiments of the present disclosure, determining a target point on the corrected travel path may comprise:

using a knee point on the corrected travel path as the target point.

The knee point on the corrected travel path refers to a point at which the travel direction of the travel path has a relatively large deflection degree; therefore, by selecting the knee point as the target point, when the catheter travels to a corresponding position in the artery, it may be adapted to deformation of the shape of the artery at the knee point position, such that the catheter may travel more easily in the artery. Meanwhile, the knee point is also a point with a relatively large curvature on the travel path, such that when the catheter indwells in the artery, it may play a good support role to the catheter.

In the embodiments of the present disclosure, the determining a knee point on the corrected travel path as the target point may comprise:

determining the deflection angle of the travel direction of the corrected travel path at the knee point, wherein the deflection angle refers to the included angle between the travel direction when the travel path advances the target point and the corrected travel direction;

if the deflection angle exceeds a deflection threshold, using the knee point as the target point.

As shown in FIG. 8, $p_n$ is a knee point on the travel path.

In the embodiments of the present disclosure, if the corrected travel path includes preset segments which are simulated and connected segment by segment in sequence, the determining a knee point on the corrected travel path as the target point may comprise:

using a connecting point which connects two adjacent preset segments on the corrected travel path as the knee point.

As shown in FIG. 8, the corrected travel path includes preset segments $P_{n-1}P_n$ and $P_nP_{n+1}$ connected in succession; then the target point $p_n$ is the connecting point which connects $P_{n-1}P_n$ and $P_nP_{n+1}$, i.e., the knee point of the travel path. The travel direction of the preset segment $P_{n-1}P_n$ is $\vec{v1}$, and the travel direction of the preset segment $P_nP_{n+1}$ is $\vec{v2}$. The plane in the figure is a plane determined based on $\vec{v1}$ and $\vec{v2}$.

In the embodiments of the present disclosure, the catheter may be shaped after the bend angle of the bend is determined, which may specifically comprise:

disposing the bend in vapor to be fumigated;

disposing the fumigated bend into cold water for shaping.

By virtue of the method for simulating the catheter shape as described in the embodiments of the present disclosure, the resulting simulated and corrected travel path of the catheter may characterize the actual travel path of the catheter in the artery and may also reflect the substantial shape of the catheter indwelling in the lumen of the artery, wherein the corrected travel path highly agrees with the shape of the artery. Therefore, the technical solutions as described in the embodiments may determine the catheter shape more accurately, and such shaped catheter has a better stability when indwelling in the artery. Additionally, the catheter maintains morphological consistency with the artery in the three-dimensional space. For example, when the artery has a spiral shape, the catheter may travel spirally and upwardly in adhesion to the arterial wall; therefore, when the catheter determined based on this corrected travel path is traveling in the artery, it may be bent to fit with the shape of the artery so as to enter the artery more easily.

Figure 9:
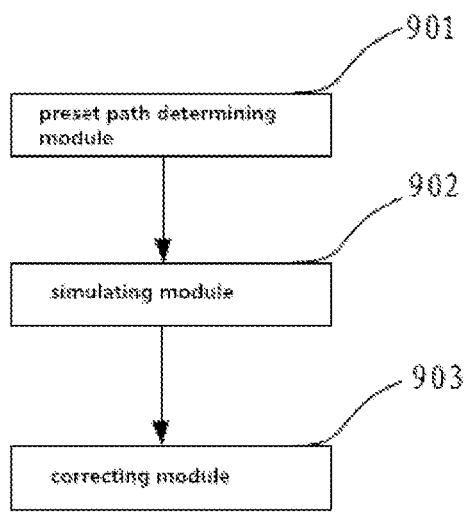
FIG. 9 shows a structural schematic diagram of an apparatus for simulating a travel path of a catheter in a blood vessel according to an embodiment of the present disclosure.

FIG. 9 shows a structural schematic diagram of an apparatus for simulating a travel path of a catheter in a blood vessel according to an embodiment of the present disclosure.

The apparatus for simulating a travel path of a catheter in a blood vessel according to an embodiment of the present disclosure may comprise:

a preset path determining module 901 configured for determining a preset path for the catheter to travel in a target artery segment based on extending direction of an artery, wherein the target artery segment refers to an artery segment which is subsequently subjected to catheter path simulation and includes an aneurysm;

a simulating module 902 configured for simulating the travel path of the catheter in a lumen of the target artery segment; and a correcting module 903 configured for correcting the travel path based on the preset path to obtain the corrected travel path.

Optionally, the determining a preset path for the catheter to travel in a target artery segment based on extending direction of an artery further comprises:

determining a preset path in the lumen of an aneurysm segment to simulate a catheter travel path based on extending direction of the artery, wherein the aneurysm segment to simulate a catheter travel path refers to a simulated segment of an artery segment including aneurysm;

simulating the travel path of the catheter in a lumen of the target artery segment; and correcting the travel path based on the preset path to obtain the corrected travel path;

Optionally, the determining a preset path for the catheter to travel in a target artery segment based on extending direction of an artery comprises:

determining the target artery segment of a three-dimensional shape based on the extending direction of the artery; and determining the preset path in the lumen of the target artery segment of the three-dimensional shape.

Optionally, the simulating the travel path of the catheter in a lumen of the target artery segment comprises:

simulating, segment by segment in sequence, the travel path of the catheter in a lumen of the target artery segment based on preset segments;

and the correcting the travel path based on the preset path comprises:

correcting each of the preset segments based on the preset path.

Optionally, the correcting each of the preset segments based on the preset path comprises:

determining an end position of the preset segment based on the travel direction of the preset segment; and correcting at least one of the end position and the travel direction of the end position based on a deviation between the end position and the preset path.

Optionally, the simulating, segment by segment in sequence, the travel path of the catheter in a lumen of the target artery segment based on preset segments further comprises:

determining a start position of a to-be-simulated preset segment based on the corrected end position;

determining the travel direction of the to-be-simulated preset segment based on the corrected travel direction of the end position; and simulating the travel path of the catheter in the to-be-simulated preset segment based on the determined start position and the determined travel direction of the to-be-simulated preset segment.

By virtue of the technical solutions described in the embodiments of the present disclosure, the resulting simulated and corrected catheter path may characterize the actual travel path of the catheter in the artery and may also reflect a substantial shape of the catheter indwelling in the lumen of the artery, wherein the corrected travel path highly agrees with the shape of the artery. The process of the catheter's entering the artery may be simulated based on the corrected travel path, such that the travel path of the catheter in the artery, as well as the shape and position of the catheter indwelling in the artery, may be determined more accurately, such that the operator may determine more intuitively whether the catheter may be inserted to a specified position in the blood vessel, which enhances convenience.

Based on the same inventive concept, an embodiment of the present disclosure provides an electronic device, comprising: at least one processor and a memory, the memory storing a program which, when being executed by the at least one processor, performs the following steps:

determining a preset path for the catheter to travel in a target artery segment based on extending direction of an artery, wherein the target artery segment refers to an artery segment which is subsequently subjected to catheter path simulation and includes an aneurysm;

simulating the travel path of the catheter in a lumen of the target artery segment; and correcting the travel path based on the preset path to obtain a corrected travel path.

Particularly, other functions of the processor may also refer to the disclosure in the embodiments above, which will not be detailed here one by one.

Based on the same inventive concept, an embodiment of the present disclosure provides a computer-readable storage medium, comprising a program used in combination with the electronic device, wherein the program may be executed by the processor to perform steps of:

determining a preset path for the catheter to travel in a target artery segment based on extending direction of an artery, wherein the target artery segment refers to an artery segment which is subsequently subjected to catheter path simulation and includes an aneurysm;

simulating the travel path of the catheter in a lumen of the target artery segment; and correcting the travel path based on the preset path to obtain a corrected travel path.

Various embodiments in the specification are described in a progressive manner, and same or similar parts between various embodiments may be referenced to each other, while each embodiment focuses on differences from other embodiments. Particularly, for a system embodiment, because it is substantially similar to the method embodiment, it is described relatively simply. Relevant parts may refer to the method embodiments.

What have been described above are only preferred embodiments of the present disclosure, not for limiting the present disclosure; to those skilled in the art, the present disclosure may have various alterations and changes. Any modifications, equivalent substitutions, and improvements within the spirit and principle of the present disclosure should be included within the protection scope of the present disclosure.

We claim:

1. A method for simulating a travel path of a catheter in a blood vessel, comprising:

obtaining, by a processor, three-dimensional imaging data of a target artery segment including an aneurysm, wherein the target artery segment refers to an artery segment which is subsequently subjected to computational catheter path simulation and includes an aneurysm;

constructing, by the processor, a three-dimensional model of the target artery segment based on the three-dimensional imaging data using computational modeling algorithms;

determining, by the processor, a preset path for the catheter to travel in a lumen of the three-dimensional model of the target artery segment based on an extending direction of an artery;

simulating, by the processor, the travel path of the catheter in the lumen of the three-dimensional model of the target artery segment;

correcting, by the processor, the travel path based on the preset path to obtain the corrected travel path; and determining, by the processor, a shape of the catheter based on the corrected travel path;

wherein the determining, by the processor, of the preset path comprises:

determining an intervention segment between the catheter entry on the artery and the aneurysm, wherein the intervention segment refers to a catheter portion which is connected with a catheter tip portion and inserted into the artery after the catheter tip portion is inserted into the aneurysm; and determining the preset path in the lumen of the target artery segment for the intervention segment based on the extending direction of the artery, wherein the determining of the shape of the catheter comprises:

determining a bend angle and a bend direction of at least one bend part of the catheter along the extending direction of the catheter, wherein the bend part refers to a bend of the catheter when shaping the catheter, manufacturing a physical catheter based on the determined bend angle and bend direction such that the catheter is designed for the patient's unique arterial anatomy.

2. The method according to claim 1, wherein the determining a preset path for the catheter to travel in a target artery segment based on extending direction of an artery comprises:

determining, by the processor, the target artery segment of a three-dimensional shape based on the extending direction of the artery; and determining, by the processor, the preset path in the lumen of the target artery segment of the three-dimensional shape.

3. The method according to claim 1, wherein the simulating the travel path of the catheter in a lumen of the target artery segment comprises:

simulating, by the processor, segment by segment in sequence, the travel path of the catheter in a lumen of the target artery segment based on preset segments;

and the correcting the travel path based on the preset path comprises:

correcting, by the processor, each of the preset segments based on the preset path.

4. The method according to claim 3, wherein the correcting each of the preset segments based on the preset path comprises:

determining, by the processor, an end position of the preset segment based on the travel direction of the preset segment; and correcting, by the processor, at least one of the end position and the travel direction of the end position based on a deviation between the end position and the preset path.

5. The method according to claim 4, wherein the simulating, segment by segment in sequence, the travel path of the catheter in a lumen of the target artery segment based on preset segments comprises:
- determining, by the processor, a start position of a to-be-simulated preset segment based on the corrected end position;
- determining, by the processor, the travel direction of the to-be-simulated preset segment based on the corrected travel direction of the end position; and
- simulating, by the processor, the travel path of the catheter in the to-be-simulated preset segment based on the determined start position and the determined travel direction of the to-be-simulated preset segment.

* * * * *